United States Patent [19]

Siegmeier et al.

[11] Patent Number: 4,762,954
[45] Date of Patent: Aug. 9, 1988

[54] CONTINUOUS METHOD FOR THE PRODUCTION OF 1,2-DIOLS

[75] Inventors: Rainer Siegmeier, Bad Homburg; Günther Prescher, Hanau; Helmut Maurer, Rodenbach, all of Fed. Rep. of Germany

[73] Assignee: Degussa Aktiengesellschaft, Frankfurt am Main, Fed. Rep. of Germany

[21] Appl. No.: 82,516

[22] Filed: Aug. 7, 1987

[30] Foreign Application Priority Data

Aug. 23, 1986 [DE] Fed. Rep. of Germany ....... 3628674

[51] Int. Cl.$^4$ ...................... C07C 29/10; C07C 31/20
[52] U.S. Cl. ..................................... 568/867; 568/700
[58] Field of Search ................................ 568/867, 700

[56] References Cited

U.S. PATENT DOCUMENTS

| | | | |
|---|---|---|---|
| 2,650,940 | 9/1953 | Young | 568/867 |
| 2,686,817 | 8/1954 | Copes et al. | 568/867 |
| 4,599,467 | 7/1986 | Kerten et al. | 568/867 |
| 4,626,603 | 12/1986 | Siegmeier et al. | 568/867 |

FOREIGN PATENT DOCUMENTS 2023601  1/1980  United Kingdom ............... 568/867

*Primary Examiner*—J. E. Evans
*Attorney, Agent, or Firm*—Cushman, Darby & Cushman

[57] ABSTRACT

The continuous production of 1,2-diols by means of saponification of aliphatic, linear or branched epoxides with 8–30 carbon atoms or high molecular weight cycloaliphatic epoxides with water and acidic catalyst at pressures of 1–5 bar using a vapor-liquid mixture of a solubilizing agent which is stationary in a column. The yields obtained are high and exhibit a high degree of purity. The water added can be recycled as such.

9 Claims, 1 Drawing Sheet

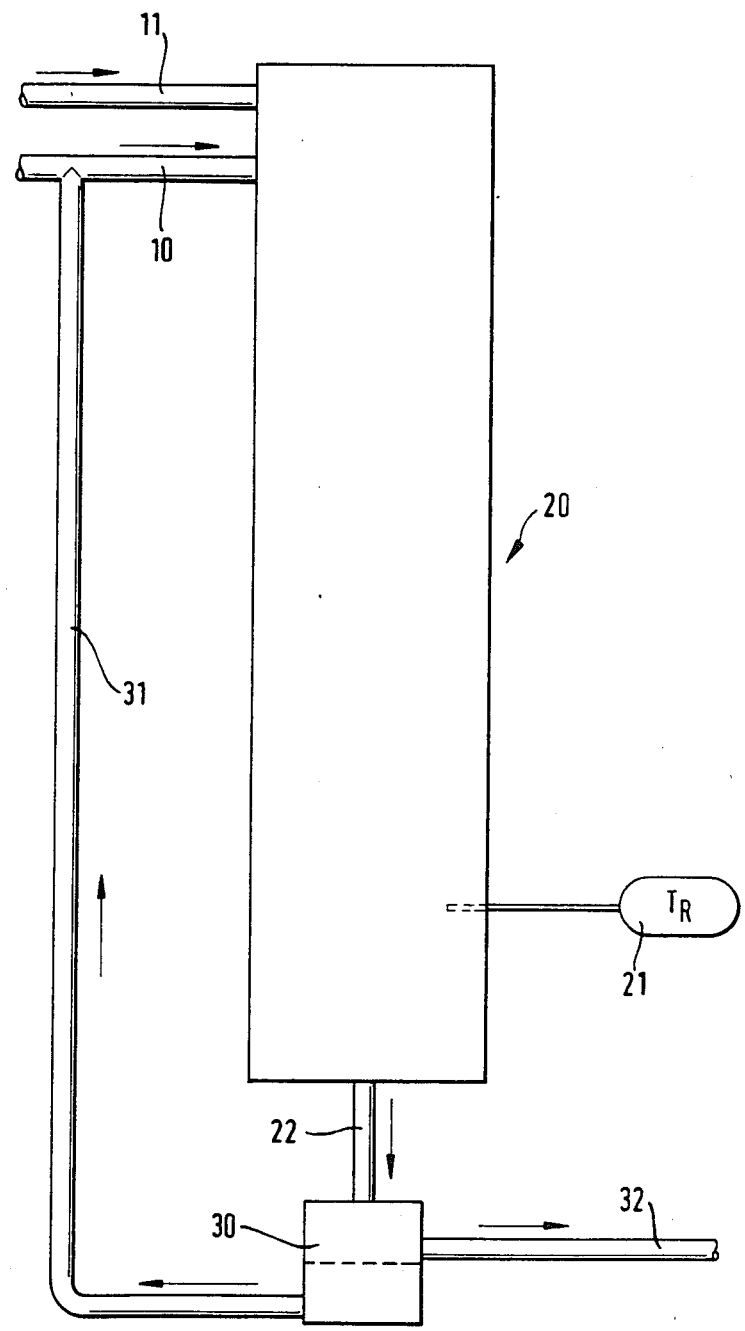

CONTINUOUS METHOD FOR THE PRODUCTION OF 1,2-DIOLS

The present invention relates to the continuous production of vicinal diols, that is, of diols whose hydroxyl groups are on adjacent carbon atoms, by saponification of the corresponding epoxides.

BACKGROUND OF THE INVENTION

Vicinal diols are useful as components in the production of polyesters and polyurethanes as well as in the cosmetic and pharmaceutical industry.

They are produced, inter alia, by saponification of their corresponding epoxides. This saponification is catalyzed both by the addition of acids (cf. for example the state of the art in U.S. Pat. No. 3,576,890) and of alkalis (cf. for example DE-OS No. 17 93 247; DE-OS No. 22 03 806) and of salts of aliphatic mono or polycarboxylic acids (DE-OS No. 22 56 907) as well as primary, secondary or tertiary amine salts or ammonium salts (EP-OS No. 0 025 961).

It is also known that the acid acting as catalyst can be produced by means of the addition of esters of lower carboxylic acids and their hydrolysis to alcohol and acids (U.S. Pat. No. 3,576,890).

The saponification can be performed in a purely aqueous medium or in the presence of solubilizing agents such as water-soluble ketones or cyclic ethers (DE-OS No. 22 56 907). The last-named patent explains that difficulties arose in a purely aqueous hydrolysis of epoxides without the presence of solubilizing agents, if one did not use ethylene oxide but rather high molecular weight water-insoluble epoxides. The result was long reaction times, moderate yields and poor selectivity.

The difficulties were naturally especially great in the saponification of epoxides or epoxide cuts which contained 8 to 30 carbon atoms due to their poor water solubility. Therefore, the discontinuous saponification of long-chain epoxides to the corresponding diols was performed according to European patent specification EU-PS No. 25 961 using special catalysts, namely ammonium salts of organic or inorganic acids. The amount of catalysts in relation to the epoxide used was high; in spite of the use of an autoclave, the reaction times were around 4 to 6 hours generally and the yields were only moderate.

SUMMARY OF THE INVENTION

The object of the present invention is to provide a method for the continuous saponification of such high molecular weight epoxides in which a purely aqueous system is used at normal temperatures and low pressures and the process is carried out in the presence of an acidic catalyst.

In accordance with the invention, it has been found that this object can be achieved in the saponification of aliphatic straight-chain or branched-chain epoxides which contain 8-30 carbon atoms and cycloaliphatic epoxides as well as the corresponding epoxide cuts with water at pressures of 1-5 bar in the presence of an acidic catalyst and of a solubilizing agent which is miscible with water, if both the water and the acidic catalyst as well as the epoxide to be saponified are allowed to enter at the top of a column and to flow through the vapor-liquid mixture of the solubilizing agent in the column. In the proces of the invention, the temperature is set in the lower part of the column, above the column bottom, such that the condensed solubilizing agent flowing down from the top part of the column evaporates again before reaching the bottom of the column and condenses again at the top of the column, and the saponification of the epoxide to the corresponding diol occurs essentially in the gas-liquid phase of the solubilizing agent. The diols produced by the process and the aqueous acidic phase collect at the bottom of the column, are removed from the column and are processed in a conventional manner.

BRIEF DESCRIPTION OF FIGURE OF DRAWING

The drawing illustrates schematically apparatus for carrying out the method of the invention.

DETAILED DESCRIPTION OF PREFERRED EMBODIMENTS

The solubilizing agent used in the method of the invention must have the following properties: It must be miscible with water and be inert in relation to the aqueous acidic phase, the epoxide starting material and the diol produced. Its boiling point or boiling range may not be above that of water at the column pressure of 1–5 bar prevailing at the bottom of the column. It preferably forms one or several minimum azeotropes with water, that is, whose boiling point is in a pressure range of 1–5 bar below the boiling point of water. In particular, diethers from diethylene glycols such as e.g. dioxane, which forms an azeotrope with water at 88° C. at 1 bar, have proven themselves useful as solubilizing agents in the method of the invention.

Diethylene glycol dimethylether, which has an azeotropic boiling point of 99° C. at 1 bar and tert. butanol which has a boiling point of 80° C. at 1 bar are also very suitable.

The amount of solubilizing agent to be used is a function of the type and size of the column and must be determined by testing.

The method of the invention can be performed in a conventional distillation column which is operated with total reflux during the saponification.

Filling bodies or bottoms, e.g. bell bottoms can be used as column inserts.

The bottom of the column can basically be heated by a conventional evaporator; a forced-circulation reboiler is preferred.

The bottom of the column is heated in such a manner that the condensed solubilizing agent, which flows back into the lower part of the column, re-evaporates almost entirely before it reaches the bottom.

A temperature measuring point is used for this purpose which regulates the heating of the bottom in such a manner that the solubilizing agent re-evaporates practically completely, as was stated, before reaching the bottom. The location and required temperature of the measuring point must be selected so that practically no solubilizing agent can be found in the bottom, even in the case of brief fluctuations of the temperature profile. The correct location for measuring the temperature must also be determined by a manual test prior to operation of the column. The bottom temperature is regulated in such a manner that. if it drops below a required temperature determined in the manual tests, the heating of the bottom is increased until the lower limit value of the temperature is at least reached and preferably exceeded.

The column bottom contains only the aqueous acidic phase and the diol formed. It has been determined by gaschromatographic analysis that it is practically free of the solubilizing agent. The diol formed is separated from the aqueous phase by phase separation. It then normally exhibits a degree of purity which is sufficient for its further use. It can be purified by distillation, but this is necessary only in the case of special purity requirements.

Suitable epoxides with 8-30 carbon atoms are epoxides of the formula

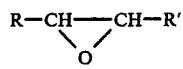

in which R is an alkyl residue and R' an alkyl residue or hydrogen. R and R' can be alkyl residues containing, in total, up to 28 carbon atoms and R and R' contain, in total, at least 6 carbon atoms.

Suitable acidic catalysts are mineral acids and strong organic acids, e.g. sulfuric acid, perchloric acid, methane sulfonic or toluene sulfonic acid. Sulfuric acid or perchloric acid are preferable.

The concentrations of the aqueous acids are between 0.1 and 5% by weight, preferably between 0.5 and 2% by weight.

The ratio of epoxide to water is generally around 1:2 to 1:10, preferably around 1:5 to 1:10. The acidic catalyst is preferably added together with the water into the top part of the column, although a separate addition of both is possible.

When the column is put into operation, a mixture of water and solubilizing agent is placed in the bottom in such an amount that the solubilizing agent evaporates as azeotrope completely from the bottom, but the bottom heating can be operated at the same time. The mixture is heated to a boil and after a stationary vapor-liquid equilibrium has been reached, the bottom is checked by gas chromatography to see if it is free of solubilizing agent.

Then the epoxide is introduced continuously via line 11 at the top of column 20 (see FIG. 1). The aqueous phase, which consists of fresh water and preferably also of the acidic circulating water which accumulates during the separation of the diol, also enters at the top of column 20 via line 10. The aqueous phase preferably contains in any case, that is, with or without circulating water, the acidic catalyst. Epoxide as well as water and acidic catalyst flow together through the vapor-liquid phase of the solubilizing agent inside column 20. The bottom contents are conducted continuously from the bottom of column 20, via line 22, into phase separation vessel 30, the aqueous acidic phase is conducted as circulating water via line 31 back into line 10 at the top of column 20 and the diol is removed via line 32. 21 is the temperature measuring point.

The method of the invention makes it possible to obtain long-chain diols continuously in high yields of about 90% or more. Very low saponification pressures such as atmospheric pressure or pressures only slightly above atmospheric pressure can be used. This enables the use of moderate saponification temperatures. Because of the low temperature and pressure requirements, it is possible to use simple apparatus such as, for example, conventional distillation columns.

The method of the invention is also rendered environmentally safe because of the possibility of recycling the water used for saponification, and it is also very economical since no waste is generated. Another essential feature is the fact that the solubilizing agent remains in the column as a stationary phase and is not to be found in the saponified product; therefore, it is not necessary to separate it from this mixture. Finally, the diols obtained exhibit a degree of purity which is sufficient for their main types of use.

The invention is illustrated in more detail in the Examples listed in table I. After 0.5-1 h the conversion was nearly quantitative. The examples were performed during 1 h.

TABLE I

| Epoxide | Epoxide Addition g/h | Amount of Water Added g/h | Catalyst/ | Amount* | Solubilizing Agent | Yield % |
|---|---|---|---|---|---|---|
| 1-octene oxide | 128.4 | 827 | HClO$_4$ | 0.6% | Dioxane | 93.0 |
| 1-octene oxide | 127.2 | 828.7 | H$_2$SO$_4$ | 0.6% | Dioxane | 90.3 |
| 1-dodecene oxide | 185 | 846.6 | HClO$_4$ | 1.0% | Dioxane | 92.2 |
| 1-dodecene oxide | 103.3 | 906.3 | H$_2$SO$_4$ | 1.0% | Dioxane | 89.0 |
| 1-dodecene oxide | 185.6 | 842.2 | H$_2$SO$_4$ | 1.0% | t-butanol | 87.1 |
| 1-octadene oxide | 182 | 866.2 | HClO$_4$ | 1.5% | Dioxane | 91 |

*Catalyst concentration in relation to the amount of aqueous phase

What is claimed is:

1. A continuous method for the production of a 1,2-diol in which an aliphatic straight-chain or branched epoxide which contains 8-30 carbon atoms or a cycloaliphatic epoxide or an epoxide cut is saponified with water at a pressure of 1-5 bar in the presence of an acidic catalyst and of a solubilizing agent which is miscible with water and inert in relation to the aqueous phase, the epoxide starting material and the diol formed, the boiling point or boiling range of said solubilizing agent being not above that of water at the prevailing column pressure of 1-5 bar, said method comprising introducing the water and the acidic catalyst as well as the epoxide to be saponified at the top of a column and flowing through the vapor-liquid mixture of the solubilizing agent located in the column and maintaining the temperature in the lower part of the column, above the column bottom, sufficiently high that the condensed solubilizing agent flowing down from the top part of the column re-evaporates before reaching the bottom and recondenses at the top of the column and the saponification of the epoxide to the corresponding diol occurs essentially in the gas-liquid phase of the solubilizing agent within the column, whereby the diols produced by the process and the aqueous acidic phase accumulate at the bottom of the column, and recovering the diols from the bottom of the column.

2. A method as set forth in claim 1 in which a solubilizing agent is used which forms one or several minimum azeotropes with water and whose boiling point, at a pressure range of 1-5 bar, is below the boiling point of water.

3. A method as set forth in claim 1 in which a diether of diethylene glycol is used as solubilizing agent.

4. A method as set forth in claim 1 in which dioxane is used as solubilizing agent.

5. A method as set forth in claim 1 in which diethylene glycol dimethylether is used as solubilizing agent.

6. A method as set forth in claim 1 in which a tertiary alcohol is used as solubilizing agent.

7. A method as set forth in claim 6 in which tert. butanol is used as solubilizing agent.

8. A method as set forth in claim 1 in which the ratio of epoxide to water is 1:2 to 1:10.

9. A method as set forth in claim 8 in which the ratio of epoxide to water is 1:5 to 1:10.

* * * * *